United States Patent [19]
Koutrakis et al.

[11] Patent Number: 5,571,945
[45] Date of Patent: Nov. 5, 1996

[54] METHOD AND APPARATUS TO MEASURE PARTICULATE MATTER IN GAS

[76] Inventors: Petros Koutrakis, 24 Ashmont Rd., Wellesley, Mass. 02181; Peng-Yau Wang, Nine Peabody Terr., Cambridge, Mass. 02138; Jack M. Wolfson, 428 Centre St., Jamaica Plain, Mass. 02130; Constantinos Sioutas, Four Goodwin Pl., Apt. #4, Boston, Mass. 02114

[21] Appl. No.: 403,321

[22] Filed: Mar. 13, 1995

[51] Int. Cl.$^6$ ..................................................... G01N 15/06
[52] U.S. Cl. ........................................ 73/28.03; 73/28.04
[58] Field of Search ............................... 73/28.01, 28.03, 73/28.04, 865.5

[56] References Cited

U.S. PATENT DOCUMENTS

| | | | |
|---|---|---|---|
| 2,675,697 | 4/1954 | Quynn et al. | 73/28.04 X |
| 3,351,759 | 11/1967 | Rich | 73/28.01 X |
| 3,888,112 | 6/1975 | De Leeuw et al. | 73/28.01 X |
| 4,550,591 | 11/1985 | Cox et al. | 73/28.03 X |
| 4,960,568 | 10/1990 | Matsumoto et al. | 73/23.2 X |

OTHER PUBLICATIONS

Cahill et al., "Analysis of Respirable Fractions in Atmospheric Particulates Via Sequential Filtration," *J. Air Pollut. Control Assoc.*, 27:675–678 Jan. 1977.

Daley and Lundgren, "The performance of piezoelectric crystal sensors used to determine aerosol mass concentration." *Am Ind. Hyg. Assoc. J.* 36:518–532 Jul. 1975.

Gupta et al., "Effect of Humidity and Particle Hygroscopicity on the Mass Loading Capacity of High Efficiency Particulate Air (HEPA) Filters," *Aerosol Sci. and Technol.* 19:94–107 (1993).

Heidman, "Review: Aerosol Fractionation by Sequential Filtration of Nuclepore Filters" *Atmos. Environ.* 15(6):891–904 (1981).

Japuntich et al., "Experimental Results of Solid Monodisperse Particle clogging of Fibrous Filters," *J. Aerosol. Sci.* 25(2):385–393 (1994).

John et al. "Anomalous Filtration of Solid Particles by Nuclepore Filters," *Atmos. Environ.* 12:1555–1557 (1978).

Liu et al., "Performance of HEPA and ULPA Filters," *Particle Technology Laboratory Publication No. 565*, Presented at the *31st Annual Technical Meeting of the Institute of Environmental Sciences*, Las Vegas, Nevada, Apr. 29–May 2, 1985, Publ. Jan. 185.

Liu and Pui, "On the Performance of the Electrical Aerosol Analyzer," *J. Aerosol Sci.* 6:249–264 (1975).

Lundgren et al., "Aerosol Mass Measurement Using Piezoelectric Crystal Sensors," *Fine Particles*, edited by B. Y. H. Liu, Academic Press, New York pp. 486–510 (1976).

Sem et al., "Performance of the piezoelectric microbalance respirable aerosol sensor," *Am. Ind. Hyg. Assoc. J.* 38:580–588 Nov. 1977.

Macias and Husar, "A Review of Atmospheric Particulate Mass," *Fine Particles*, edited by B. Y. H. Liu, Academic Press, New York pp. 536–564 (1976).

Manton, "The Impaction of Aerosols on a Nuclepore Filter," *Atmos. Environ.* 12:1669–1675 (1978).

(List continued on next page.)

*Primary Examiner*—Michael J. Brock
*Attorney, Agent, or Firm*—Lyon & Lyon

[57] ABSTRACT

Apparatus for measuring the amount of particulate matter in a gas having a gas supply, a first particulate matter collector downstream of the gas supply and in gaseous communication with the gas supply, and a second particulate matter collector downstream of the gas supply and in gaseous communication with the gas supply. Gas from the gas supply to the second particular matter collector is passed through a particle remover to remove particulate matter prior to contact of gas from the gas supply with the second particulate matter collector. A pressure sensor is provided to measure differential pressure between the first particulate matter collector and the second particulate matter collector, and at least one pump to cause gas to pass from the gas supply to the first particulate matter collector and the second particulate matter collector.

19 Claims, 5 Drawing Sheets

OTHER PUBLICATIONS

Melo and Philips, "Aerosol Size Spectra by Means of Nuclepore Filters," *Environ. Sci. and Technol.* 9:560–564 Jan. 1974.

Novick et al., "The Effect of Solid Particle Mass Loading on the Pressure Drop of HEPA Filters," *J. Aerosol Sci.* 23:657–665 (1992).

Parker and Buzzard, "A Filtration Model For Large Pore Nuclepore Filters *Aerosol Sci."* 9:7–16 1978.

Pope et al., "Respiratory Health and $PM_{10}$ Pollution," *Am. Rev. Res. Dis.* 144:668–674 (1992).

Schwartz and Dockery, "Increased Mortality in Philadelphia Associated with Daily Air Pollution Concentrations[1-4]," *Am. Rev. Resp. Dis.* 145:600–604 (1992).

Sioutas et al., "Particle loss in glass honeycomb denuders," *Aerosol Science & Technology* 21(2):137–149 (1994).

Smith and Philips, "Inertial Collection of Aerosol Particles at Circular Aperture," *Environ. Sci. and Technol.* 9:564–568 Jun. 1975.

Spurny et al., "Aerosol Filtration by Means of Nuclepore Filters: Structural and Filtration Properties," *Environ, Sci. and Tech.* 3(5):453–468 May 1969.

Swift, "Direct–Reading Instruments for Analyzing Airborne Particles," *Air Sampling Instruments,* edited by S. V. Hering. American Conference of Governmental Industrial Hygienists, Inc., Cincinnati, OH 00. 477–506 (1989).

Whitby, "Electrical Measurement of Aerosols," *Fine Particles,* edited by B. Y. H. Liu, Academic Press, New York pp. 584–624 (1976).

Whitby and Svendrup, "California Aerosols: Their Physical and Chemical Characteristics," *The Character of Origins of Smog Aerosols,* Hidy et al. eds., John Wiley & Sons, Inc., New York, New York, pp. 477–517 (1980).

Willeke and Liu, "Single Particle Optical Counters: Principle and Applications" *Fine Particles,* edited by B. Y. H. Liu, Academic Press, New York pp. 698–729 (1976).

Holländer et al. "Sensitive detection of particulate air pollutants by means of metal–coated Nucleopore filters" Proceedings of the 12th Int. Colloqium on Atmospheric Pollution, May 1976, pp. 477–485.

METHOD AND APPARATUS TO MEASURE PARTICULATE MATTER IN GAS

BACKGROUND OF THE INVENTION

This invention relates to methods for measuring particulate matter in a gas, such as for environmental sampling.

Epidemiological studies in the U.S.A. and abroad have shown associations between mortality and morbidity and human exposures to ambient particulate matter (Schwartz and Dockery, *Am. Rev. Resp. Dis.* 145:600–604 1992; Pope et al., *Am. Rev. Res. Dis.* 144:668, 1992). To date, there is limited knowledge about the physical or chemical property of particulate matter that are responsible for these health effects. Whether the particulate matter is a surrogate for an unknown toxicant or is the responsible agent itself for the observed health effects, there is an increasing interest in developing accurate measurements in the near future. Currently, the agencies are receiving the permitted ranges for ambient particles. Although no decision has been made about the form of the new standard regarding the size cutoff and concentration level parameters, there is a mandate for the use of a reference or equivalent method.

The majority of current particle mass measurement methods use a size selective inlet to remove particles above a certain size, usually 10 μm in diameter ($PM_{10}$). There is a large discrepancy between the different methods. This is due to the effects of wind velocity on the inlet performance. These effects are more pronounced for coarse particles, those with aerodynamic diameter between 2.5 and 10 μm. Thus, if the revised standard decreases the particle size, this problem will be minimized. Most of the available data on $PM_{10}$ and $PM_{2.5}$ have been obtained using gravimetric methods. The collected particles, usually on Teflon filters, are weighed using microbalances under constant specified temperature and relative humidity conditions. Gravimetric methods are not sensitive enough to measure samples within less than 24 hours. In addition, attempting to obtain a better time resolution for ambient particle concentrations routinely for large monitoring networks is presently cost-prohibitive and impractical. Therefore, development of continuous particle monitors will be important in order to establish comprehensive monitoring networks that will provide information on temporal and spatial variability of particle mass concentration in a cost-effective way.

To date, there are several direct-reading instruments; an excellent review of such instruments has been given by Swift, *Air Sampling Instruments*, edited by S. V. Hering. American Conference of Governmental Industrial Hygienists, Inc., Cincinnati, Ohio (1989). Nevertheless, there are a number of questions regarding the quality of data these instruments can provide. Some methods use the optical properties of ambient particles to measure their mass (e.g., the mini-RAM instrument, nephelometers, instruments measuring the Coefficient of Haze, etc.). However, because the chemical composition and size of particles varies significantly with time and space, it is difficult to establish a constant relationship between particle mass and extinction coefficient. These methods may be of limited use, i.e. for studies of fine aerosols in locations where the composition of particles is not expected to vary significantly. An advantage in some of these methods is that collection of particles on a filter media may not be required. Interactions between particles on filter media and/or particle to gas conversions and vice-versa can result in significant overestimation or underestimation of particulate mass. This problem applies to both continuous and integrated methods that collect particles on filter media.

Another continuous particle mass method is the beta-gauge (Macias and Husar, in *Fine Particles*, edited by B. Y. H. Liu, Academic Press, New York, 1976). The attenuation of the beta rays passing continuously through the filter is proportional to the particle mass collected on the filter. However, the relationship between mass and energy absorption depends to some extent on the particle composition. In addition, a radioactive material is required as an energy source. Therefore, the beta-gauge method may not be the method of choice for the future.

Quartz crystal piezobalances measure particulate mass directly through particle impaction on an oscillating quartz surface (Lundgren et al., in *Fine Particles*, edited by B. Y. H. Liu, Academic Press, New York, (1976)). More specifically, a disk of quartz oscillates in an electric circuit at a highly stable resonant frequency which decreases in direct proportion to the particulate mass impacting and adhering onto the sensor. Although such instruments have been used with some success in providing direct readings of aerosol mass concentrations, they suffer from several potential shortcomings. First, the high oscillating frequency of the quartz crystal can lead to saturation effects. Second, the fact that particle collection is done by impaction leads to collection uncertainties. Several investigators (Daley and Lundgren, "The performance of piezoelectric crystal sensors used to determine aerosol mass concentration." *Am Ind. Hyg. Assoc. J.* 36:518, (1975); Lundgren *Am. Ind. Hyg. Assoc. J.* 38:580–588, (1977)) found that the frequency change for a given incremental mass deposit on the sensor does not remain constant as the sensor becomes loaded. This is due to the change in the particle collection patterns over time. Some aerosols, such as $CaCO_3$ deposit uniformly in the beginning, but as the loading increases, the freshly depositing particles tend to deposit near the center of the sensor, probably because of the change in the electrical conductivity of the collection surface. Other types of aerosols, such as $Fe_2O_3$, while they initially deposit uniformly over the sensor, as loading increases, the impacting particles do not adhere as well to the surface. As a result, the frequency of a loaded crystal does not change as much as that of a clean crystal for the same increment of mass, thus the loaded crystal senses a lower concentration than the actual. Finally, aerosols consisting of carbonaceous particles which are composed of long stable chains of very small primary particles cannot be measured with piezobalances; the chain aggregates contact the sensor at 2 to 3 points with most of the particulate mass waving above the sensor surface. This observation was confirmed with experiments using black carbon particles as the test aerosol to be collected on the piezobalance. The response of the instrument became non-linear within few minutes after the beginning of the experiments.

The Tapered Element Oscillating Microbalance (TEOM®) is a recently developed method that originally appeared to be very promising (Patashnick and Rupprecht, "Continuous PM-10 Measurements Using the Tapered Element Oscillating Microbalance" *J. Air Waste Manage. Assoc.* 41:1079–1083 (1991)). According to this method, the air sample is heated up to 50° C. to remove moisture, and particles are subsequently collected on a TEFLON® filter that oscillates at the top of a metal rod. The amplitude of the oscillation decreases as the mass of the particles collected on the filter increases. Although this method is highly sensitive, its measurements are subject to a number of interferences;

significant losses occur for semivolatile organic and inorganic compounds that in some areas can represent relatively large fraction of the total particulate matter. This problem is more pronounced for $PM_{2.5}$, which includes unstable compounds such as ammonium nitrate and carbonaceous aerosols. For areas such as California and large urban environments, this method would significantly underestimate particle mass concentrations. Also, as the composition of the air sample changes, the partitioning of air pollutants between the gas and particle phase changes, therefore adsorption and/or desorption processes can take place on the filter (depending on whether the air sample becomes more or less polluted). Due to the sensitivity of the method, these phenomena can cause either negative or positive artifacts. The gains and losses of mass on the filter are a serious problem, not just of the TEOM®, but of any method that collects particles on a filter over a prolonged period of time (on the order of days). In the case of the TEOM®, the filter media are usually exposed for a week. Finally, this method presents oscillations in its response which cancel out if a large number of measurements are added to determine a multi-hour concentration estimate; however, over shorter time intervals the measurement errors due to this oscillation can exceed 20–30%.

Other direct-reading methods to measure particle concentration include optical and electrical counters. Optical counters make use of the interaction between light and particles. A review on the theory of optical aerosol behavior and its application to particle measurement is discussed by Willeke and Liu, "Single Particle Optical Counters: Principle and Applications" *Fine Particles*, edited by B. Y. H. Liu, Academic Press, New York (1976). Most of the optical systems count light pulses scattered from particles that flow, one by one, through an intensely illuminated zone. Some of their limitations are low sampling flow rates, and the fact that the smallest detectable particle size is about 0.3 μm. Since there may be a significant fraction of the fine ambient particulate mass associated with particles smaller than 0.3 μm, optical counters are not adequate to measure the entire atmospheric particle range.

Electrical counters are based on charging the sampled aerosols and measuring the ability of particles to traverse an electrical field. Most of these counters draw particles through a cloud of either unipolarly or bipolarly charged ions, and each of the particles acquire a quantity of charge that is simply related to its size. Subsequently, the particles are drawn into a radially symmetric electrical field where particles smaller than a certain size, which depends on the intensity of the field, are collected onto the walls of the collecting device. By changing the field voltage, the particle size distribution can be obtained (Liu and Pui, "Unipolar Charging of Aerosol Particles in the Continuum Regime", *J. Aerosol Sci.*, 6:249 (1975); Whitby, "Electrical Measurement of Aerosols", *Fine Particles*, edited by B. Y. H. Liu, Academic Press, New York, (1976)). The most widely used instrument of this category is the Differential Mobility Analyzer manufactured by TSI Inc. (St. Paul, Minn.). This technology has been proven to be useful in generating monodisperse aerosol in the size range 0.01–1.0 μm. However, particles larger than about 1.0 μm in diameter cannot be accurately measured by this instrument because the relationship between particle charge and particle size is not monotonic for particles larger than 1.0 μm.

Using the Differential Mobility Analyzer in conjunction with an optical counter would make it possible to measure a broad size range of atmospheric particles. Nevertheless, even in this case, the combined optical/electrical counter may still suffer from two shortcomings. The first shortcoming arises from the fact that these counters measure the number distribution of particles which they subsequently convert to volume distribution. To measure the mass distribution one needs to know the particle density which is known to vary depending on the sampling location and the sampling period (e.g., winter vs. summer). The second shortcoming is intrinsic to converting a number to a volume distribution. The number distribution of ambient particles is dominated by ultrafine particles, in the size range 0.01–0.1 μm. The coarser the particles, the smaller their number concentration becomes. However, when converting a number to volume distribution, a 1.0 μm particle is weighed as much as $10^3$ 0.1 μm particles and $10^6$ 0.01 μm particles. Consequently, this conversion is bound to lead to counting errors because a low background concentration of coarse particles (which may just be within the noise of the instrument) will be converted to a significant fraction of the volume distribution.

To conclude, there is a great need for the development of a continuous particle mass measuring instrument. As long as the health effects studies cannot identify the chemical constituents or physical properties of particulate matter that are responsible for the observed morbidity and mortality, we ought to include in particle measurement all individual components. Continuous mass measuring methods should be robust for both stable species (e.g., sulfates and dust) as well as unstable species (e.g., ammonium nitrate, chloride, and SVOCs). Furthermore, the effects of relative humidity and temperature on particle mass measurement should be addressed.

As discussed below, particles should preferably be conditioned to 40% RH (when ambient RH exceeds 40%) to minimize the interference due to water vapor. The air sample should preferably not be heated because unstable compounds can easily volatilize resulting in an underestimate of particle mass. In situ aerosol measurements are very desirable since they are free from particle interference and adsorption and desorption problems. However, if use of filter media is necessary, the collection surface should preferably not be used for more than 20–30 minutes in order to avoid filter mass gain or loss problems. The continuous method should either regenerate the collection surface or use a new surface for each measurement.

The purpose of the present invention is to provide a continuous mass measurement method that incorporates all of the features mentioned above. Mass concentration measurement is based on monitoring the pressure drop across a porous membrane filter (or its equivalent) over a period of time. As will be discussed below, this pressure drop is a linear function of the particle mass concentration of the sampled air.

SUMMARY OF THE INVENTION

This invention provides an apparatus for real time measurement of the amount of particulate matter in a gas. Depending on the amount of particulate matter in the gas being measured, such information can be provided on a continuous basis, or at least on an hourly basis. This compares with those devices noted above where such information is provided only on a daily or lesser basis. Such an improvement over the existing apparatuses is dependent on the use of measurement of pressure differentials between a reference filter and a test filter. Applicant makes use of the reduced ability of a filter to pass gas when particulate matter is present on that filter, compared to when the filter is clean. The amount of particulate matter is directly related to the reduction in gaseous flow through the filter.

In a first aspect, the invention features an apparatus for measuring the amount of particulate matter in a gas. The apparatus includes a gas supply (which may be a simple inlet or a more complex sourcing means), a first particulate matter collector downstream of the gas supply in gaseous communication with the gas supply, and a second particulate matter collector downstream of the gas supply in gaseous communication with the gas supply. Gas from the gas supply to the second particular matter collector is passed through a particle remover to remove particulate matter prior to contact of gas from the gas supply with the second particulate matter collector. A pressure sensor is also provided to measure the differential pressure between the first particulate matter collector and the second particulate matter collector. At least one pump is also present to cause gas to pass from the gas supply to the first particulate matter collector and the second particulate matter collector.

In preferred embodiments, the apparatus has a plurality (at least two or three) of pumps, where at least one pump is configured and arranged to pump gas from the gas supply to the first particulate matter collector and another pump is designed to pump gas from the gas supply to the second particulate matter collector; the first and/or second particulate matter collector is a filter, e.g., a nucleopore filter; the apparatus further has a dryer (e.g., a diffusion or air dryer) to adjust the humidity of gas from the gas supply to the first and/or second particulate matter collectors, e.g., to about 40% relative humidity; the first particulate matter collector is moveable and is configured and arranged to be automatically replaced a plurality of times with a replacement first particulate matter collector; the second particulate matter collector is moveable and is configured and arranged to be automatically replaced with a replacement second particulate matter collector; e.g., the first or second particulate matter collector is provided as a streaker; gas from the gas supply is prefiltered, e.g., with an impactor, to remove particulate matter larger than 10 or 2.5 microns prior to contact with either the first or second particulate matter collectors; and the apparatus further has a computer system configured and arranged to continuously or discontinuously record the differential pressure between the first and second particulate matter collectors.

In a second aspect, the invention features a method for measuring the amount of particulate matter in a gas, by providing an apparatus as described above, causing gas to pass from the gas supply to the first and second particulate matter collectors, and measuring the pressure differential between the first and second particulate matter collectors as an indication of the amount of the particulate matter in the gas.

In preferred embodiments, the procedure is performed at least once per hour; and the first particulate matter collector is replaced every one to twenty-four hours.

Other features and advantages of the invention will be apparent from the following description of the preferred embodiments thereof, and from the claims.

DESCRIPTION OF THE PREFERRED EMBODIMENTS

The drawings will first briefly be described.

Drawings FIG. 1 is a graph showing the relationship between pressure and particle concentration measured by a device of the present invention in a collection efficiency test (PSL particle, 2 μm pore, 8 LPM).

Figure 2:
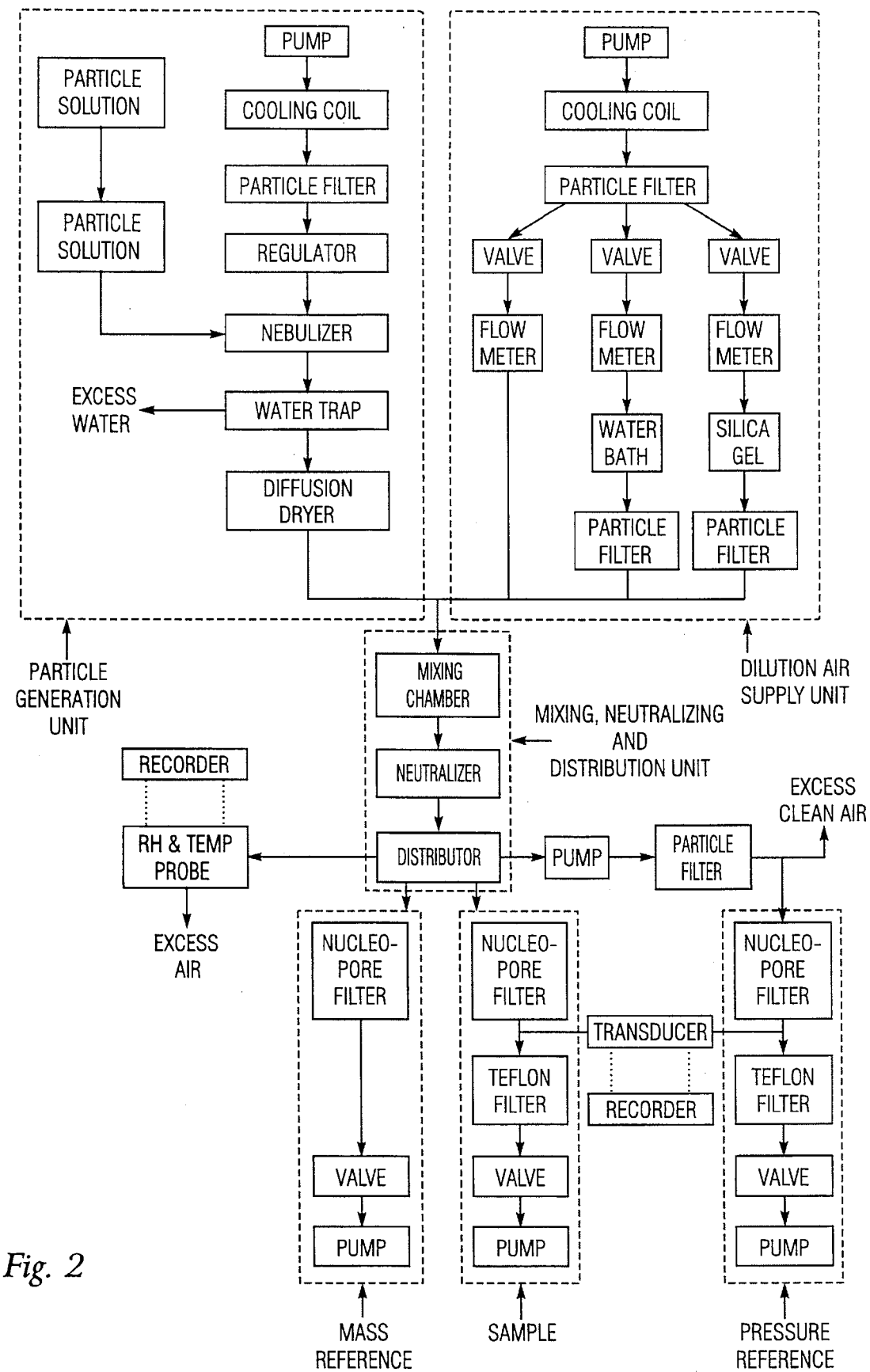
FIG. 2 is a schematic diagram of apparatus to demonstrate the utility of the present invention.
Figure 3:
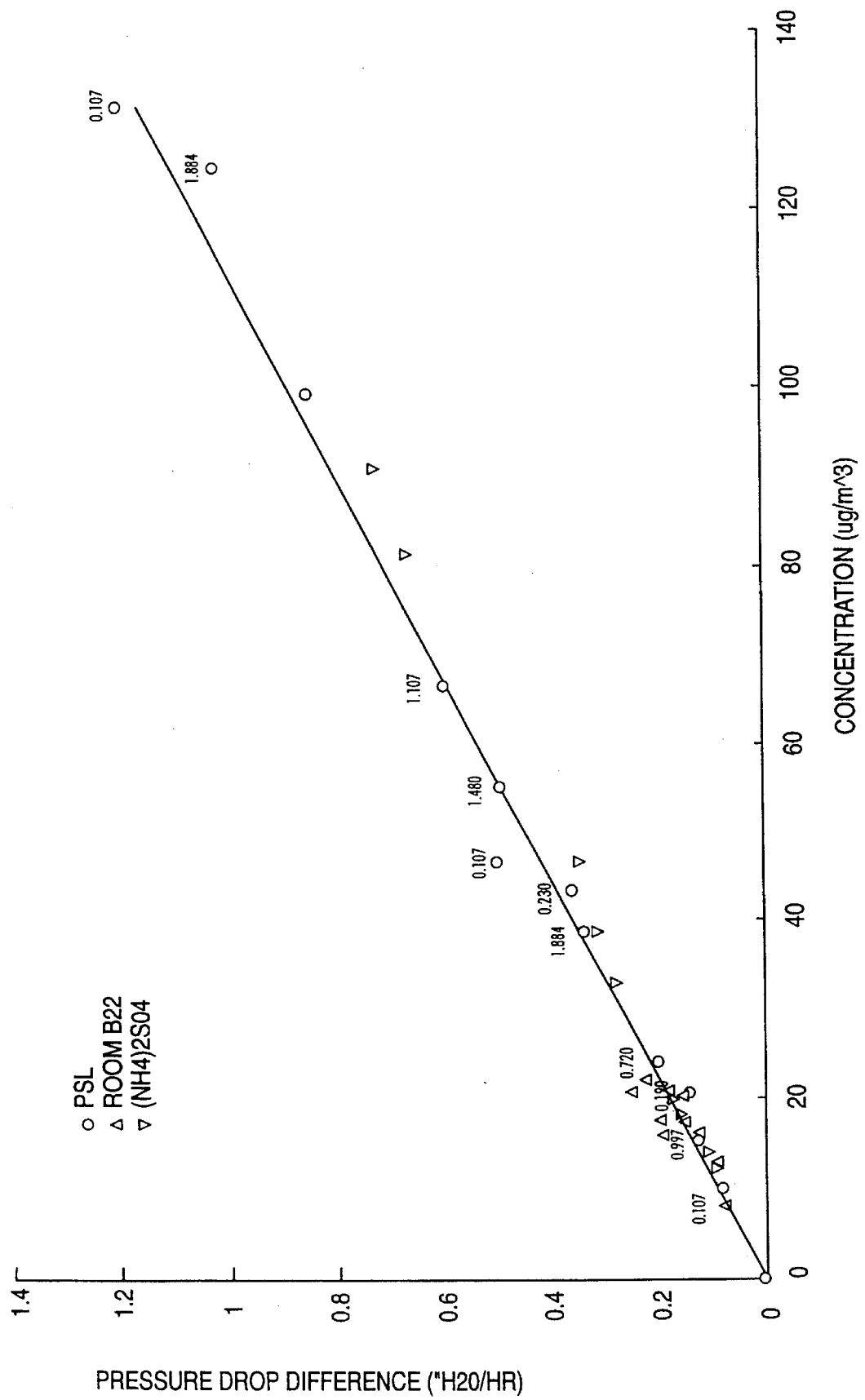
FIG. 3 is a graph showing collection efficiency of a sampling device operating as described below. The graph plots pressure drop vs concentration (2 μm pore at 8 LPM, pressure drop at the first hour).
Figure 4A:
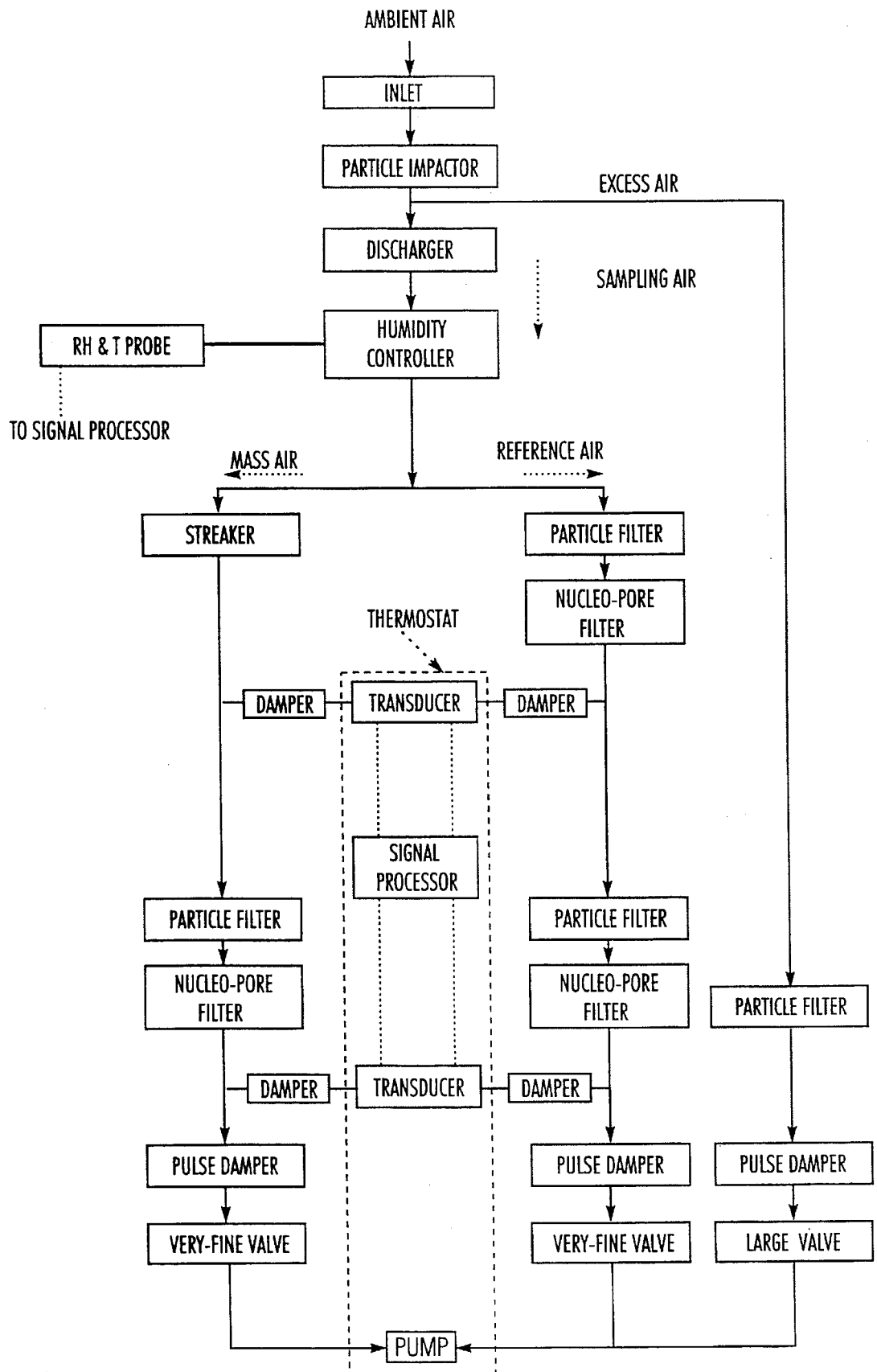
Figures 1, 4B:
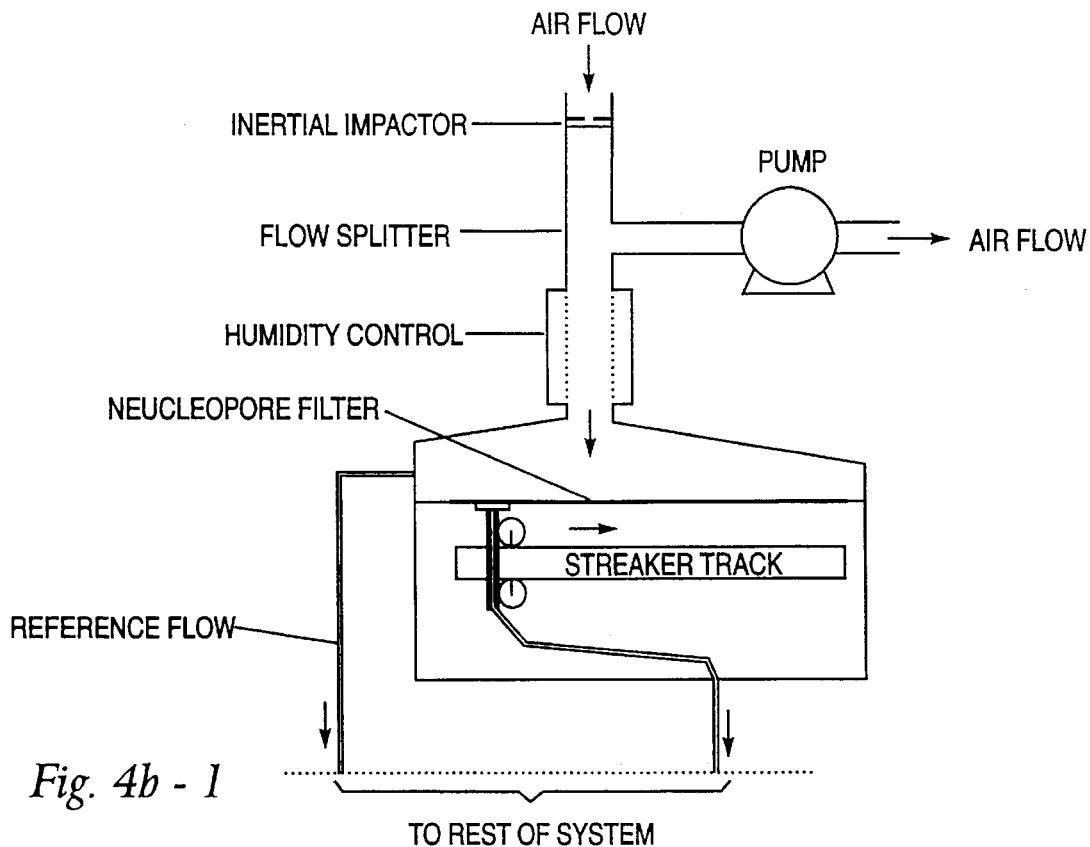
Figures 2, 4B:
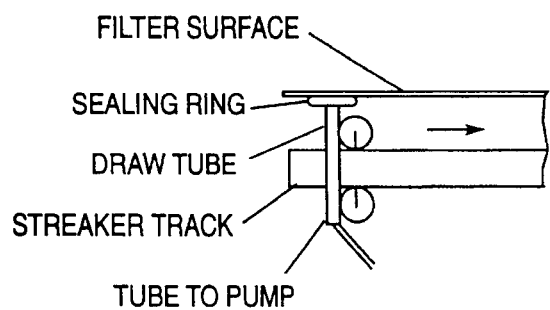
Figures 3, 4B:
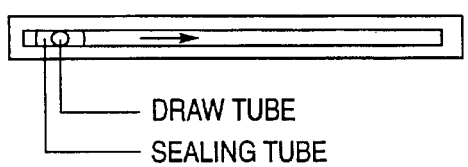

FIGS. 4a and 4b (1–3) are schematic diagrams of a sampler. FIG. 4a is a schematic showing various components of a CAMM system. FIG. 4b(1–3) is a detailed schematic of a streaker component of the device in FIG. 4a. FIG. 4b-2 is a side view of the streaker component and FIG. 4b-3 is a top view of the streaker component.

Following is an example of the invention using a nucleopore filter as the particle collection medium. This is but one example of a useful collection device of this invention. Those in the art will recognize that other collection apparatus can be used as described below, and are within the invention.

Nucleopore Filters

Nucleopore filters are thin (6–12 μm) non-hygroscopic polycarbonate membranes with circular pores normal to the surface. The pores are distributed randomly over the surface and are very uniform in size (the geometric standard deviation is 1.1; Heidam, "Review: Aerosol Fractionation by Sequential Filtration with Nuclepore Filters", *Atmos. Environ.* 15(6):891–904, (1981). The theoretical prediction for the particle collection efficiency of these filters has been based on models that assumed uniformly distributed arrays of equal size pores (Pich, "Impaction of Aerosol Particles in the Neighborhood of a Circular Hole", *Colln. Czech. Chem. Commun.* 29:2223–2227 (1964); Spurny et al., "Aerosol Filtration by Means of Nuclepore Filters: Structural and Filtration Properties", *Environ. Sci. and Tech.* 3(5):453–468 (1969)). Although their pore volume is smaller, Nuceopore filters have about the same flow rate-pressure drop relationships as membrane filters of comparable pore size. In addition, they are non-hygroscopic, which makes it possible to use them for sensitive gravimetric analysis. They can also be analyzed for light transmittance, or filter segments can be cut for microscopy.

The main mechanisms affecting particle capture (Spurny et al., "Aerosol Filtration by Means of Nuclepore Filters: Structural and Filtration Properties", *Environ. Sci. and Tech.* 3(5):453–468 (1969)) are: 1) impaction of large particles on the filter surface due to deflection of the air streamlines; 2) interception of particles whose size is comparable to the pore size; 3) diffusion of small particles to the pore walls; 4) retention of particles larger than the pores (sieve effect); and 5) electrostatic effects. Electrostatic effects are the only mechanism that has not been thoroughly studied. However, according to Smith and Philips, "Inertial Collection of Aerosol Particles at Circular Aperture", *Environ. Sci. and Technol.* 9:564–568 (1975) is of no practical importance. Spurny and Pich first considered the cumulative efficiency due to individual retention mechanisms. The three main capturing mechanisms have been assumed to be independent, e.g., impaction, interception, and diffusion. Since the pioneering studies by Pich, "Impaction of aerosol particles in the neighborhood of a circular hole." *Colln. Czech. Chem. Commun.* 29:2223–2227, (1964), several authors have attempted to derive formulae that express the different collection mechanisms in terms of the particle size, and design and operating parameters of the filters (e.g., pore size, length, face velocity, filter porosity).

The collection efficiency due to impaction was given by Pich, supra (1964) by solving the Navier-Stokes equations of particle motion in the proximity of the filter pores. The Stokes number has been extensively used in the earlier literature (Spurny et al., "Aerosol Filtration by Means of Nuclepore Filters: Aerosol Sampling and Measurement", *Environ. Sci. and Technol.* 3:464–468 (1969); Spurny and Madeleine, "Analytical Methods for Determination of Aerosols by Means of Membrane Filters. XIX. Efficiency Measurement of Nuclear Pore Filters by Means of Latex Aerosols", *Colln. Czech. Chem. Commun.* 36:2857–2866 (1971); Melo and Philips, "Aerosol Size Spectra by Means of Nuclepore Filters", *Environ. Sci. and Technol.* 9:560–564 (1974)). However, the Stokes equation was based on the erroneous assumption of a parabolic velocity profile and that the axial component of the fluid velocity remains constant. In fact, there is a very substantial increase in the axial component as the fluid merges and enters the pore. The effect of the merging streamlines would be a substantial decrease in particle impaction onto the surface between the pores.

To model the collection efficiency due to interception, as a first approximation a "plug" flow in the pore was assumed, e.g. particle flow per unit area was considered uniform over the whole pore area. However, several authors argued that the flow profile near the entrance of the pore is to a good approximation that of laminar flow in a tube, implying that there is little flow near the wall of the pore and therefore interception should be smaller than the prediction of the "plug" flow (Heidam, "Review: Aerosol Fractionation by Sequential Filtration of Nuclepore Filters" *Atmos. Environ.* 15(6):891–904 (1981)). Several expressions have been suggested, in which the "plug" flow efficiency is modified by multiplying by an "appropriate" coefficient, see, e.g., Spurny and Madeleine, supra (1971).

In an attempt to better understand and predict particle collection, some studies provided numerical solutions for the particle and fluid flow fields (Smith and Philips, supra, 1975; Manton, "The Impaction of Aerosols on a Nuclepore Filter", *Atmos. Environ.* 12:1669–1675 (1978)). In the former study, an expression for the efficiency by the combined mechanisms of inertia and interception is derived. Of particular interest is the observation that particle impaction occurs on the pore edge instead of the space between pores for particles with Stokes numbers less than about 10. For such particles, the collection efficiency appears to be an almost linear function in same size ranges. The experimental study by John et al. "Anomalous Filtration of Solid Particles by Nuclepore Filters", *Atmos. Environ.* 12:1555–1557 (1978) provided further support to the enhanced impaction-interception theory by Smith and Philips, supra, (1975). Large particles (size range 2–8 µm) were sampled by a 8 µm pore size nucleopore filter at face velocities of about 6 cm/s. The Stokes numbers for the above particle and filter parameters ranged from 0.9 to 15, and the collection efficiency was well-fitted by a modified interception model.

John et al. supra (1978) examined the deposition patterns on the filter through a microscope and found that the particles were deposited mostly on the periphery of the pores. Thus, despite the fact the sampled particles were large enough to impact onto the filter surface, according to the original analysis of Pich, supra (1964), interception appeared to be the dominant capture mechanism.

The collection efficiency due to diffusion has been computed by two different equations, depending on the value of the coefficient of diffusive collection, see, e.g., Twomey *Observ. Puy. Dome.* 10:173–180, (1962).

The various theoretical attempts to model particle collection efficiency of nucleopore filters are not entirely in agreement, mainly due to the different approximations used by each study to solve the Navier-Stokes equations for the air flow field, as well as the different assumptions on diffusion mechanisms. However, on a qualitative basis, these studies described quite well the importance of various design and operating parameters of the filer on the collection efficiency. One of the main conclusions were that increasing the face velocity lead to sharper impaction separation, in addition to increasing the efficiency for smaller particles. The most important feature, however, that was observed in every study on nucleopore filters was the presence of a central minimum in the collection efficiency vs. particle size curves, where neither impaction nor diffusion are effective in capturing particles. Based on this observation, Spurny et al, "Aerosol Filtration by Means of Nuclepore Filters: Aerosol Sampling and Measurement" *Environ. Sci. and Technol.* 3:464–468 (1969) noted that nucleopore filters in series could make even finer discrimination than when used singly, since a nearly monodisperse aerosol can be extracted from a polydisperse aerosol stream with such a filter series. This gave rise to a sampling technique called "sequential filtration" (Cahill et al., "Analysis of Respirable Fractions in Atmospheric Particulates Via Sequential Filtration", *J. Air Pollut. Control Assoc.*, 27:675–678 (1977)). Although a few studies attempted to use sequential filtration for classifying particles into discrete size ranges (Melo and Philips, supra, 1975; Parker and Buzzard, "A Filtration Model For Large Pore Nuclepore Filters" *Aerosol Sci.* 9:7–16, (1978)), this method has not been used extensively, probably due to the fact that the collection efficiency curves are not steep enough to result in a high-resolution particle classification.

Pressure Drop in Nucleopore Filters

Pressure drop in filters is an important parameter, since it provides a criterion for assessing filter performance. A useful filter is one that gives the highest collection efficiency with the least pressure drop. The effect of particle mass loading on the pressure drop has been examined in previous studies for fiber filters (for example, Rudnick and First, "Specific Resistance (K2) of Filter Dust Cakes: Comparison of Theory and Experiments", *Third Symposium on Fabric Filters for Particulate Collection*, EPA600/7-789-087, (1978); Novick et al., "The Effect of Solid Particle Mass Loading on the Pressure Drop of HEPA Filters" *J. Aerosol Sci.* 23:657–665, (1992); Japuntich et al., "Experimental Results of Solid Monodisperse Particle Clogging of Fibrous Filters", *J. Aerosol. Sci.* 25(2):385–393 (1994)), and pore membrane filters (Rubow, "Submicrometer Aerosol Filtration Characteristics of Membrane Filters" *Ph. D. Dissertation* Univ. of Minnesota (1981)). These studies showed clearly a linear relationship between pressure drop across the filter and the mass loading. In addition, these studies showed that the slope of the pressure drop-loading curve depends on the size of the collected particles. More specifically, that slope is inversely proportional to the particle size.

The literature on pressure drop versus mass loading as a function of particle size is not nearly as extensive for nucleopore filters. Spurny et al. "Aerosol filtration by means of nuclepore filters: aerosol sampling and measurement." *Environ. Sci. and Technol.* 3:464–468, (1969) and Spurny and Madeleine G. "Analytical methods for determination of aerosols by means of membrane filters. XIX. Efficiency measurement of nuclear pore filters by means of latex aerosols. *Colln. Czech. Chem. Commun.* 36:2857–2866.", (1971) studied the time development of pressure drop in nucleopore filters in an attempt to understand clogging mechanisms. Three different clogging stages were identified. In the first stage, pressure drop increases gradually with time, due to the gradual decrease in the pore size caused by particle deposition. In the second stage, a complete filling of the pores occurs, accompanied by a sharp increase in the pressure drop. In the final stage, air is filtered through heaps of particles and since the thickness of this particulate plug grows slowly, the pressure drop increases more slowly. However, this study did not examine the dependence of pressure drop versus mass loading on the particle size in a systematic manner. A theoretical model was developed to predict the pressure drop as a function of particle and filter parameters. The Hagen-Poiseuille equation was used to express the pressure drop. An empirically-based correction for solid particles was made to account for the fact that, unlike liquid particles, solid particles do not coat the pore wall uniformly upon deposition, thus influencing the particle layer thickness and geometry. See, Spurny et al. supra (1969). Such an equation assumes that 100% of the particles approaching the filter are responsible for raising the pressure drop through it. This does not mean only that the particle collection efficiency is 100% but that particles are collected only inside the pores. A particle collected due to impaction onto the area between the pores of the filter cannot increase the pressure drop through the filter. The pressure drop prediction derived by the above equation was never confirmed experimentally.

Clogging of the pores and subsequent increase in the pressure drop has been attributed to either deposition by diffusion to the pore walls or to interception of larger particles on the pore edges. Previous studies, however, in which the particle deposition patterns was examined through a microscope, showed that deposition primarily occurs at the pore edges instead of inside the pore, especially at face velocities higher than 5 cm/s (Spurny et al., supra (1969); Parker et al., supra (1978)). Local accumulation of particles on the pore edge leads to the formation of clusters, which further enhance particle deposition onto the already accumulated clusters. Eventually the clusters close the pore, and after this stage particles deposit in a heap above the pore. Consequently, diffusion as a deposition mechanism should not affect the pressure buildup in a nucleopore filter as much as interception.

An alternative theory could be applied to predict and explain the main mechanism for increasing the pressure drop in a nucleopore filter with loading, especially during the first stage of filtration. Contrary to the theory developed by Spurny et al. supra (1969), which considers deposition throughout the tube of the pore responsible for increasing the pressure drop, the new theory only considers phenomena occurring at the pore edge responsible for the pressure drop.

The flow can be modelled as flow through a tube with an obstruction due to particle deposition. Typically, flow obstruction has been used to model the flow and pressure drop through partially open valves (International Organization for Standardization, "Measurement of Fluid Flow by Means of Orifice Plates, Nozzles, and Venturi Tubes Inserted in Circular Cross-Section Conduits Running Full", *ISO Report DIS*-5167, Geneva, Switzerland, (1976)). The pressure drop through an obstruction such as that shown in FIG. 1 can be described by the following equation:

$$\Delta P = K/Re \ V^2 \tag{1}$$

where Re is the Reynolds number in the obstructed part of the tube (Re=V d $\rho/\mu$), d is the diameter of the obstructed part of the tube, $\rho$ and $\mu$ are the density and viscosity of the air, and V the velocity in unobstructed part of the tube (e.g., the pore velocity). The values of coefficient K depend largely on the particular configuration and the flow conditions and they can be determined experimentally to fit the data. The pore velocity is given by the following equation:

$$V = U \frac{D^2}{d^2} \tag{2}$$

where U is the face velocity of the filter and D the nominal pore diameter of the filter. The diameter of the obstructed part of the pore can be calculated by considering an overall reduction in the available surface of the tube due to the deposition of particles over time. For a given particle size, the available open surface of the pore can be written in the following form:

$$\pi d^2/4 = \pi(D^2/4) - n_p \pi(d_p^2/4) \tag{3}$$

where $n_p$ is the number of particles that have deposited on the walls of the pore and $d_p$ their diameter. The number of particles that have deposited over a period of time, t, can be calculated as follows:

$$n_p = n_0 t (Q/N_f) \eta \tag{4}$$

where $n_0$ is the number concentration of particles in the sampled air (particles/cm$^3$), $N_f$ is the number of filter pores, Q is the sampling flow rate, and $\eta$ is a collection efficiency factor accounting for the fact that only the particles depositing on the edge of the pore are responsible for increasing the pressure drop by reducing the pore surface. Particles depositing due to interception but not due to impaction on the area between the pores or diffusion inside the pore will lead to an increase in the pressure drop.

Since the volume concentration of an aerosol, $c_v$, is related to its number concentration through the following equation:

$$c_v = n_0 \ (\pi/6) \ d_p^3 \tag{5}$$

equation (4) can be rewritten in the following form:

$$n_p = 6c_v/(\pi d_p^3) \ t \ (Q/N_f) \eta \tag{6}$$

and the open (or available) pore surface area can be written in the following form:

$$\pi d^2/4 = \pi(D^2/4) - (\pi d_p^2/4) \ 6 \ c_v/(\pi d_p^3) \ t \ (Q/N_f) \eta \tag{7}$$

Combining equations 2–7, equation (1), expressing the pressure drop across a nucleopore filter, can now be written as a function of various filter and particle parameters in the following form:

$$\Delta P = K'/d^3 \tag{8}$$

where the constant K' incorporates parameters the D, K, $\rho$, and $\mu$.

As discussed above, $\eta$ is the collection efficiency due to interception, resulting in particle deposition on the pore edge. Despite the fact that there is a notable lack of an adequate theory describing interception efficiency as a function of particle size, the existing studies (Spurny et al., supra (1969); Smith and Philips, supra, (1975)) have indicated that interception can be approximated as a quasi-linear function of the particle size for ratios $d_p/D$ between 0.05 to 1.0. Thus, the collection efficiency can be approximated by the following expression:

$$\eta_R = \eta = B \ (d_p/d) \tag{9}$$

where the constant B takes values between 1 and 1.1. By combining equations (7) and (8), the following expression can be derived for the diameter of the contracted part of the tube:

$$d=[D-1.5\ c_v\ t\ Q/N_f\ B/d]^{0.5} \quad (10)$$

The importance of equation (10) lies in the fact that it shows that the diameter of the obstructed part of the tube, d, and hence the pressure drop across the Nucleopore filter, ΔP, do not depend on the particle size. This is not a surprising result if one considers the mechanisms for raising the pressure drop in a filter. For the same volumetric (or mass) aerosol concentration, smaller particles have a much larger surface area than bigger particles. On the other hand, however, larger particles are more efficiently collected by the filter compared to small particles. Thus, these two competing effects tend to cancel out the effect of particle size, thereby implying that the only parameter responsible for, increasing the pressure drop are the volume concentration and the sampling duration. Thus, by knowing the functional dependence of the pressure drop on the sampling time and the volumetric concentration, one can predict the aerosol concentration by monitoring the pressure drop across the filter as a function of sampling time. If particle density is known, the mass concentration of the aerosol can then be determined. This observation serves as the basis for developing a continuous mass monitor by measuring pressure drop across a nucleopore filter.

The problem about deriving an analytical expression describing the relation between ΔP, $c_v$ and t arise from the fact that the obstructed tube diameter, d, is not a constant, but it decreases as sampling time increases, thus the collection efficiency due to interception also depends on the sampling time (it increases with time). Hence, to be able to determine the pressure drop profile over time, equations (8) and (10) need to be solved numerically, by integration in small successive steps. At time t=0, d is set equal to D and Δp=0. After a small time increment, t (which could be on the order of a minute) the new value of d can be determined from equation (10) and the new ΔP can be determined by substituting the new d value in equation (8). The same procedure can be followed to determine the values of both d and ΔP as a function of time.

As can be seen from the results presented above, and shown in FIG. 1, there is a linear relationship between pressure drop across a test filter compared to a reference filter and the concentration of particulate matter in the gas being tested. This indicates that a relatively simple apparatus can be developed based on that described above in which gas is passed through two collection means (such as nucleopore filters) and the pressure differential between the two filters is a direct measure of the concentration of the particulate matter within the gas.

EXAMPLE 1

CAMM System

An example of a sampler useful in this invention is shown schematically in FIGS. 4*a* and 4*b* (1–3). In operation, air is drawn into the device at a total sampling flow of 10 liters/minute through a diffusion dryer that removes any excess moisture and reduces relative humidity to about 40%. (Alternatively, a humidity controller can be used.) Subsequently, the air is drawn through an impactor/inlet that removes particles larger than a certain size. This is a particle separator that can cut particles either larger than 2.5 μm or 10 μm, and avoid them getting into the system; its dimensions are 6.5 cm (diameter)×27 cm (long). A major part of the sampled air is removed at 9.5 liters/minute as excess air. The discharger is a cylindrical tube on the walls of which 8–10 polonium sources are attached to neutralize particle chargers. A humidity controller and humidity-temperature probe is provided as a hollow column that has dry air in the outer-column and the sampling air in the inner-column. Between these is a diffusion membrane that allows water molecules to diffuse into the outer-column and be carried out by the dry air. A relative humidity probe is used for the RH and temperature monitoring and the RH is controlled by regulating the flow rate of the dry air. Relative humidity is controlled at 38% to 40%. A temperature signal is output to a signal processor. Dimensions are 5 cm (diameter)×10 cm (long).

The remaining air sample (sampling air, 0.5 liters/minute) is split into two parts and drawn through two parallel sections at 0.25 liters/minute each. The first part consist of a streaker sampler, shown in detail in FIG. 4*b* (1–3), whose surface is made of a porous membrane material identical to a Nuclepore filter. For a given time period only a small portion of the streaker is open to the flow and available for particle collection. The sampling part of the streaker is connected to a pump through a draw tube and a sealing O-ring. Over the sampling period, the draw tube is steadily and slowly moved onto a threaded track, thereby exposing a new part of the filter surface to the flow. The reason for using this sampling method instead of a typical round filter is to increase the filter capacity over the desired sampling period by avoiding clogging, as well as to avoid losses due to volatilization of accumulated matter as sampling progresses. Volatilization losses are due to changes in the ambient temperature or concentration of a volatile material. An increase in the temperature or a decrease in the ambient concentration of a volatile material can cause collected material from the filter to volatilize until a new equilibrium is reached. These losses can be substantially reduced by exposing a clean collection surface to the air flow because volatilization cannot occur before the concentration on the filter reaches its saturation value. The second part is drawn through an low-pressure drop High Efficiency Particle Filter (HEPA) filter that removes all particles (6 cm diameter×15 cm long), and subsequently through a 13 mm Nuclepore polycarbonate filter whose pore size and surface area are identical to those of the open surface of the streaker (2 cm diameter×3 cm long). The pressure difference downstream the streaker and the clean (particle-free) Nuclepore filter is continuously monitored with a high sensitivity transducer (range 0–1 inches $H_2O$, accuracy=0.25% FS) connected to a signal processor. This is a multichannel digital-to-analog converter and a signal display that can handle all signal input and display all messages in a second. Dampers are provided as columns that can smooth the pressure pulse (dimensions: 6 cm (diameter)×9 cm (long)).

A HEPA filter is placed downstream the streaker and the reference Nuclepore filter and a Nuclepore filter is placed downstream the HEPA filters in each of the parallel sections. A pressure transducer identical to that used to monitor the pressure difference between the streaker and the reference Nuclepore filter is used to record the pressure difference immediately downstream the Nuclepore filters sampling clean air. The pressure difference in the first transducer is mainly due to particle loading on the streaker. This difference, however, could be affected by fluctuations in the flow rate in either section of the sampler. Since all particles have been removed from the air samples of each section prior to being drawn through the second Nuclepore filters, any pressure difference recorded by the second transducer can only be attributed to fluctuations in the flow. Thus, by subtracting the pressure reading of the second transducer from that of the first, one can measure the increase in the pressure drop across the streaker due exclusively to particle loading. Both sampling sections are connected to pulse dampers to ensure that the flow remains stable over the sampling period. These are columns that can smooth flow pulse (dimensions: 6 cm (diameter)×9 cm (long)). The transducers are differential pressure transducers with 0–2" $H_2O$ full scale and 0.25% FS resolution.

Both transducers, the signal processor and the pump are placed in a thermally controlled container to ensure that their temperature remains at 20° C. The advantage of our system over the TEOM method is that it measures particulate mass at ambient concentration and at a constant relative humidity, thereby preventing volatilization from or gas adsorption onto the collected matter.

The relationship between the pressure drop across a nucleopore filter and the aerosol mass concentration was tested in laboratory experiments.

EXAMPLE 2

Model System

The experimental setup is shown in FIG. 2. Suspensions of 2.5% by weight fluorescent yellow-green latex microspheres (Fluoresbrite, Polysciences, Warrington, Pa.) were nebulized by a pocket nebulizer (Retec X-70/N) using room air at 20 psi as described by Sioutas et. al "Particle loss in glass honeycomb denuders". *Aerosol Science & Technology,* 21 (2):137–149, (1994). The volumetric flow rate of the nebulizer was estimated to be approximately 5.5 LPM and the output was approximately 0.25 cc/min of fluorescent suspension. The nebulizer was connected to a syringe pump in order to atomize large amounts (120 ml) of the fluorescent suspension. In addition, the output of the nebulizer was maintained constant to ensure a stable atomization process. Seven different particle sizes were used: 0.06, 0.15, 0.22, 0.45, 0.77, 1.1 and 1.9 µm in diameter. The aerosol was subsequently drawn through a diffusion dryer to remove the excess moisture generated by the nebulizer. The diffusion dryer consists of two concentric cylindrical tubes, with inside diameters 2.54 and 15.24 cm, respectively, and 30.48 cm long. The space between the tubes is filled with silica gel that traps water vapor. As the aerosol is drawn through the dryer, water vapor diffuses to the walls of the smaller tube much faster than particles, hence is removed by silica gel. Thus, the aerosol exiting the dryer is completely dry and the particles assume their original size.

Subsequently, the aerosol was mixed with clean (particle-free) air with controlled relative humidity (RH). RH was controlled by adjusting the flow rates of a dry and a moist airstream. After the mixing chamber, the generated aerosol was drawn through a 1-liter cylindrical chamber where ten Polonium 210 ionizing units were placed (Staticmaster, NRD Inc.) to reduce electrostatic charges carried by the generated particles to the Boltzmann equilibrium. The aerosol was then drawn through a distributor with a temperature/relative humidity probe connected to it; part of the aerosol was drawn through a control TEFLON® filter to determine the mass concentration of the input aerosol. The rest of the generated aerosol was drawn through the sampler.

The monodispersity of the generated aerosol was confirmed by drawing samples through the TSI Scanning Mobility Particle Sizer (SMPS Model 3934, TSI Inc., St. Paul, Minn.). In addition, by monitoring the particle concentration upstream and downstream the nucleopore filter, we determined its collection efficiency as a function of particle size with an additional method to the gravimetric analysis described above.

Previous studies on fiber filters demonstrated a relationship between the relative humidity during sampling and the pressure drop across the filter (Smith et al., *Presented at 21st DOE/NRC Nuclear Air Cleaning Conference*, San Diego, August 1990, pp. 366–375; Gupta et al., "Effect of Humidity and Particle Hygroscopicity on the Mass Loading Capacity of High Efficiency Particulate Air (HEPA) Filters", *Aerosol Sci. and Technol.,* 19:94–107, (1993)). The former study showed that an increase in the relative humidity results in increasing the pressure drop across the filter, whereas the latter study concluded the opposite, i.e. a decrease in the humidity dramatically increases the pressure drop across HEPA filters. Though the exact effect of relative humidity on the pressure drop across filters is being the subject of ongoing investigation, it is evident that changes in the humidity affect the pressure drop across filters. At present, the effect of relative humidity on the pressure drop across Nucleopore filters has not been investigated. For the purpose of our example, however, we controlled the humidity of both sample and control airflows to a fixed value 40% throughout the experiments to ensure that the pressure readings are only due to changes in the mass loadings on the filters.

The relationship between pressure drop across the particle-sampling nucleopore filter per unit time as a function of particle concentration and size was investigated for various pore diameters and sampling flow rates. In addition to monodisperse fluorescent particles, polydisperse ammonium sulfate aerosols as well as indoor room air were used as the test aerosol. The ammonium sulfate particles were generated using the same nebulizer method described above.

Results

To initiate our study, we chose a 2 µm pore diameter Nucleopore filter operating at a face velocity of 12 cm/s. The choice of the pore size was made so that particle collection efficiency due to impaction/interception depends linearly on the particle size for particles in the size range 0.1–2.0 µm which comprise the fine (accumulation) mode of atmospheric aerosols (Whitby and Svendrup, "California Aerosols: Their Physical and Chemical Characteristics", *Adv. Environ. Sci. and Technol.,* 10:477, (1980)). Typically, the accumulation mode is centered around 0.3–0.8 µm diameter with a geometric standard deviation of about 2 (Hinds, *Aerosol Technology*, John Wiley & Sons, New York, (1982)). By choosing a smaller pore size (for example, D=0.4 µm), the collection efficiency of the Nucleopore filter for most of the fine atmospheric particles should be close to 100%. In addition, the sensitivity of the concentration measurements would have increased because the smaller pore size would lead to higher pressure drop readings. However, collecting most of the particles with a 100% efficiency would make the pressure drop across the filter be inversely proportional to the particle size. In fact, this relationship between pressure drop and mass loadings was observed for high-efficiency filters, such as HEPA (Novick et al., "The Effect of Solid Particle Mass Loading on the Pressure Drop of HEPA Filters", *J. Aerosol Sci.* 23(6):657–665 (1992); Japuntich et al., supra (1994)), although the physical mechanisms for increasing the pressure in those filters are presumed to differ from those in Nucleopore filters. Adjusting for a porosity value of 0.07, the choice of a pore size of 2 µm ensures that a linear relationship between the efficiency and particle size should be expected for particles in the size range 0.1–1.6 µm, at least on a theoretical basis. This range reflects the majority of fine ambient particles.

The face velocity at the streaker was chosen to be 12 cm/s as a compromise between a high enough velocity, which would make it possible to measure low concentrations within 30 minutes, and low enough velocity to keep the particle Stokes number, adjusted for p=0.07, smaller than approximately 5. The reason for keeping the Stokes number smaller than 5 was to avoid particle impaction on the surface area between the pores which would also increase the particle collection efficiency of the filter without increasing the pressure drop. Moreover, losses due to diffusion, would also be insignificant at 12 cm/s for the particles in the range 0.1–2.0 µm. The theoretical diffusion efficiency for 0.1 µm particles for the specific filter and flow parameters is 4.2% and decreases rapidly with particle size. Thus, particle deposition would occur primarily on the edge of the pore wall for the majority of particles in the size range 0.1–1.5 µm.

The collection efficiency of the 2 µm Nucleopore streaker sampler at a face velocity of 12 cm/s was determined for particles in the size range 0.1–1.8 µm and the results are shown in FIG. 3. In addition, the experimental results are compared to those predicted by the theory. The theoretical collection efficiency was determined from the following equation:

$$\eta_{tot} = \eta_R + (1-\eta_R)(\eta_D) \quad (11)$$

where $\eta_D$ and $\eta_R$ are the partial collection efficiencies due to diffusion and interception, respectively. The two capturing mechanisms have been assumed to be independent. For particles in the size range 0.1 to 2 µm and with the specific filter parameters, the collection efficiency can be represented by the following linear regression equation ($R^2=0.991$):

$$\eta_{tot} = 0.143 + 0.46 \, d_p \quad (12)$$

where $d_p$ is the particle diameter in micrometers. Thus, FIG. 3 shows that the efficiency is an almost perfectly linear function of the particle size. The regression intercept, which tends to increase efficiency at the smaller sizes, reflects diffusion as the primary capturing mechanism for these particles. FIG. 3 also shows an excellent agreement between the theoretically predicted efficiency valued and the experimental results.

The absence of impaction onto the solid filter surface as one of the capturing mechanisms has been confirmed by examining the filters in a microscope after each experiment. Even large particles, comparable to the pore size (1.5 µm in diameter or larger) deposited on the edges of the filter pores instead of the solid areas between the pores. The formation of clusters was very much like that described by Spurny et al. supra (1969) for any particle size, thus confirming previous observations that the merging of streamlines into the pores results in a radial particle movement which opposes the drift across streamlines caused by inertia. Thus, the majority of particles deposit in the vicinity of the pore edge, causing an increase in the pressure drop due to obstruction to the fluid flow.

To further investigate our hypothesis on the effect of impaction on the pressure drop, we increased the face velocity to 24 cm/s while keeping the pore size at 2 µm. The relation between pressure drop per unit time as a function of particle mass concentration was investigated using monodisperse PSL particles (0.2, 0.5, 0.72, 1.1, and 1.5 µm, respectively). For a given particle size, the pressure drop was recorded over a sampling period of 60–90 minutes. The mass concentration of the generated (input) aerosol was determined gravimetrically by weighing the control TEFLON® filter sampling in parallel to the test system, similarly to the setup shown in FIG. 2. The results of this investigation and a comparison with the initial configuration (e.g., face velocity 12 cm/s). The pressure drop per unit time and mass concentration ($\Delta P/c_m t$) remains almost constant in the initial configuration for particles in the range 0.1 to 1.88 µm. The value of ($\Delta P/c_m t$) tends to slightly decrease with particle size, possibly because the effect of increased impaction of larger particles onto the areas between pores.

Figure 1:
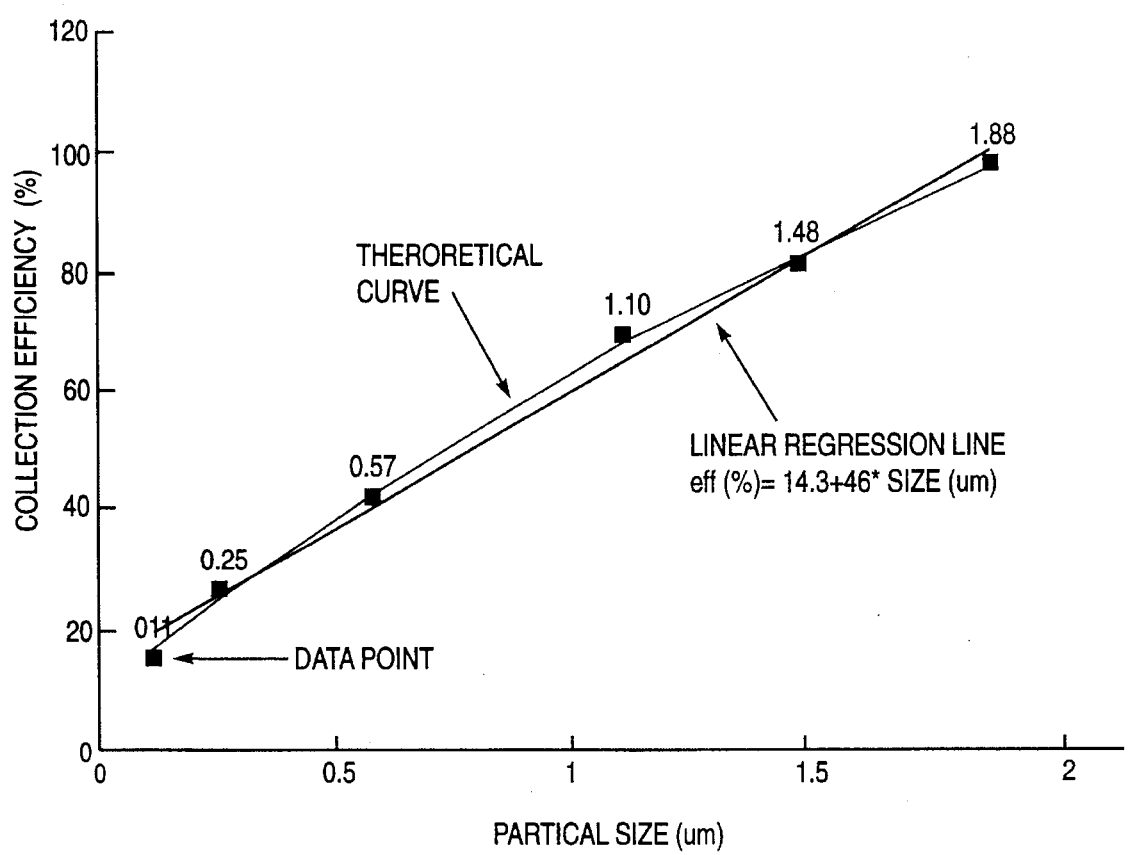

As shown in FIG. 1, there is a linear relationship between pressure drop per unit time as a function of particle mass concentration independently of particle size. The quantity ($\Delta P/c_m t$) remains almost constant in the initial configuration for particles in the range 0.1 to 1.88 µm, with an average value of 0.0088 (±0.0005) inches $H_2O$/hr/ (µg/m$^3$). The value of ($\Delta/c_m t$) tends to slightly decrease with particle size, possibly because the effect of increased impaction of larger particles onto the areas between pores. Our continuous mass monitoring method can detect as little as 5 µg/m$^3$ in about 1 hour.

The measured and estimated from the regression equation concentrations for each of the experimental tests are shown in Table 1. Aerosol mass concentrations ranged from 8.0 to 132.0 µg/m$^3$. As shown in Table 1, the estimated values from the pressure drop readings differ from the true concentrations by no more than 25%. This relative difference tends to become exaggerated at smaller concentration values, as expected. The standard error in the concentration estimate of the regression is 13.3%, thereby providing an estimate of the uncertainty in the concentration values determined by monitoring the pressure drop across the Nucleopore filter.

TABLE I

| run | size um | conc ug/m3 | slope H2O/hr | conc, est ug/m3 | err ug/m 3 | err % % | slope, est H2O/hr |
| --- | --- | --- | --- | --- | --- | --- | --- |
|  | 0.000 | 0.0 | 0.000 | −0.6 | −0.65 | 100.0 | 0.006 |
| 111 | 0.107 | 9.9 | 0.088 | 9.4 | −0.48 | −5.1 | 0.092 |
| 108 | 0.997 | 15.2 | 0.130 | 14.2 | −0.98 | −6.9 | 0.139 |
| 103 | 0.490 | 20.7 | 0.147 | 16.2 | −4.53 | −28.0 | 0.187 |
| 106 | 0.720 | 24.0 | 0.207 | 23.0 | −0.97 | −4.2 | 0.215 |
| 101 | 1.884 | 38.6 | 0.339 | 38.1 | −0.47 | −1.2 | 0.343 |
| 102 | 0.230 | 43.2 | 0.363 | 40.9 | −2.32 | −5.7 | 0.383 |
| 110 | 0.107 | 46.3 | 0.501 | 56.7 | 10.36 | 18.3 | 0.410 |
| 107 | 1.480 | 55.1 | 0.495 | 56.0 | 0.88 | 1.6 | 0.487 |
| 105 | 1.107 | 66.5 | 0.605 | 68.6 | 2.06 | 3.0 | 0.587 |
| 100 | 1.884 | 125.0 | 1.026 | 116.7 | −8.28 | −7.1 | 1.098 |
| 109 | 0.107 | 132.0 | 1.201 | 136.7 | 4.74 | 3.5 | 1.160 |
| 112 | room air | 22.1 | 0.230 | 25.7 | 3.60 | 14.0 | 0.199 |
| 113 | room air | 20.7 | 0.256 | 28.6 | 7.91 | 27.6 | 0.187 |

TABLE I-continued

| run | size um | conc ug/m³ | slope H2O/hr | conc, est ug/m³ | err ug/m 3 | err % % | slope, est H2O/hr |
|---|---|---|---|---|---|---|---|
| 114 | room air | 8.0 | 0.087 | 9.3 | 1.27 | 13.7 | 0.076 |
| 115 | room air | 12.8 | 0.098 | 10.6 | −2.15 | −20.3 | 0.117 |
| 117 | room air | 16.1 | 0.131 | 14.3 | −1.71 | −11.9 | 0.146 |
| 119 | room air | 15.9 | 0.198 | 22.0 | 6.14 | 27.9 | 0.144 |
| 120 | room air | 17.6 | 0.203 | 22.6 | 4.98 | 22.1 | 0.159 |
| 121 | room air | 20.3 | 0.163 | 18.0 | −2.29 | −12.7 | 0.183 |
| 122 | room air | 20.6 | 0.190 | 21.0 | 0.45 | 2.1 | 0.186 |
| 123 | room air | 17.3 | 0.159 | 17.5 | 0.20 | 1.1 | 0.157 |
| 124 | room air | 19.4 | 0.193 | 21.4 | 1.99 | 9.3 | 0.176 |
| 127 | (NH4)2SO4 | 13.9 | 0.110 | 12.0 | −1.92 | −16.0 | 0.127 |
| 129 | (NH4)2SO4 | 46.4 | 0.347 | 39.1 | −7.32 | −18.7 | 0.411 |
| 130 | (NH4)2SO4 | 32.8 | 0.282 | 31.6 | −1.23 | −3.9 | 0.292 |
| 131 | (NH4)2SO4 | 12.1 | 0.096 | 10.3 | −1.77 | −17.1 | 0.111 |
| 132 | (NH4)2SO4 | 38.6 | 0.314 | 35.3 | −3.33 | −9.4 | 0.343 |
| 133 | (NH4)2SO4 | 19.8 | 0.176 | 19.5 | −0.32 | −1.6 | 0.179 |
| 134 | (NH4)2SO4 | 18.2 | 0.161 | 17.8 | −0.43 | −2.4 | 0.165 |
| 135 | (NH4)2SO4 | 91.1 | 0.728 | 82.6 | −8.52 | −10.3 | 0.802 |
| 128 | (NH4)2SO4 | 81.6 | 0.670 | 76.0 | −5.61 | −7.4 | 0.719 |

Other embodiments are within the following claims.

We claim:

1. Apparatus for measuring the amount of particulate matter in a gas, comprising:

a gas supply, a first particulate matter collector downstream of said gas supply and in gaseous communication with said gas supply, a second particulate matter collector downstream of said gas supply and in gaseous communication with said gas supply wherein gas from said gas supply to said second particular matter collector is passed through a particle remover to remove particulate matter prior to contact of gas from said gas supply with said second particulate matter collector, a pressure sensor to measure differential pressure between the downstream side of said first particulate matter collector and the downstream side of said second particulate matter collector, and at least one pump to cause gas to pass from said gas supply to said first particulate matter collector and said second particulate matter collector, wherein said particulate matter collectors are non-hygroscopic polycarbonate membranes having pores normal to the surface.

2. The apparatus of claim 1 wherein said first and/or said second particulate matter collector is a nucleopore filter.

3. The apparatus of claim 1 wherein said apparatus further comprises a dryer to adjust the humidity of gas from said gas supply to said first and/or said second particulate matter collectors.

4. The apparatus of claim 3 wherein said dryer is a diffusion dryer.

5. The apparatus of claim 3 wherein said dryer adjust the relative to humidity of said gas to about 40% relative humidity.

6. The apparatus of claim 3 wherein said dryer is an air dryer.

7. The apparatus of claim 1 wherein said first particulate matter collector is moveable and is configured and arranged to be automatically replaced with a replacement first particulate matter collector.

8. The apparatus of claim 1 wherein said second particulate matter collector is moveable and is configured and arranged to be automatically replaced with a replacement second particulate matter collector.

9. The apparatus of claim 7 or 8 wherein said first or second particulate matter collector is provided as a streaker.

10. The apparatus of claim 1 comprising a prefilter wherein gas from said gas supply is prefiltered through said prefilter to remove particulate matter larger than 10 microns prior to contact with either said first or second particulate matter collectors.

11. The apparatus of claim 1 comprising a prefilter wherein gas from said gas supply is prefiltered through said prefilter to remove particulate matter larger than 2.5 microns prior to contact with either said first or second particulate matter collectors.

12. The apparatus of claim 11 wherein said prefilter is an impactor.

13. The apparatus of claim 1 wherein said apparatus further comprises a computer system configured and arranged to record the differential pressure between said first and second particulate matter collectors.

14. The apparatus of claim 1, further comprising further particulate matter collectors downstream of said first and second particulate matter collectors.

15. The apparatus of claim 14 further comprising a filter pressure sensor to measure differential pressure between said further particulate matter collectors.

16. Apparatus for measuring the amount of particulate matter in a gas, comprising:

a gas supply, a first particulate matter collector downstream of said gas supply and in gaseous communication with said gas supply, a second particulate matter collector downstream of said gas supply and in gaseous communication with said gas supply wherein gas from said gas supply to said second particular matter collector is passed through a particle remover to remove particulate matter prior to contact of gas from said gas supply with said second particulate matter collector, a pressure sensor to measure differential pressure between the downstream side of said first particulate matter collector and the downstream side of said second particulate matter collector, wherein said apparatus comprises a plurality of pumps at least one said pump configured and arranged to pump gas from said gas supply to said first particulate matter collector and another said pump to pump gas from said gas supply to said second particulate matter collector, wherein said particulate matter collectors are non-hygroscopic polycarbonate membranes having pores normal to the surface.

17. Method for measuring the amount of particulate matter in a gas, comprising the steps of:

providing an apparatus comprising a gas supply, a first particulate matter collector downstream of said gas supply and in gaseous communication with said gas supply, a second particulate matter collector downstream of said gas supply and in gaseous communication with said gas supply wherein gas from said gas supply to said second particular matter collector is passed through a particle remover to remove particulate matter prior to contact of gas from said gas supply with said second particulate matter collector, a pressure sensor to measure differential pressure between said first particulate matter collector and said second particulate matter collector, and at least one pump to cause gas to pass from said gas supply to said first particulate matter collector and said second particulate matter collector;

causing gas to pass from said gas supply to said first and second particulate matter collectors, and measuring the pressure differential between said first and second particulate matter collectors as an indication of the amount of said particulate matter in said gas, wherein said particulate matter collectors are non-hygroscopic polycarbonate membranes having pores normal to the surface.

18. The method of claim 17 wherein said measuring is performed at least once per hour.

19. The method of claim 17 wherein said first particulate matter collector is replaced every one to twenty-four hours.

* * * * *